(12) United States Patent
Washiro et al.

(10) Patent No.: US 10,158,430 B2
(45) Date of Patent: Dec. 18, 2018

(54) USING LOAD MODULATION FOR AUTHENTICATION VIA A DIELECTRIC MEDIUM, AND RELATED COMMUNICATION TERMINAL, COMMUNICATION DEVICE, COMMUNICATION METHOD AND COMMUNICATION SYSTEM

(71) Applicant: Sony Corporation, Tokyo (JP)

(72) Inventors: Takanori Washiro, Kanagawa (JP); Yoichiro Sako, Tokyo (JP); Itaru Kawakami, Kanagawa (JP); Tatsuya Inokuchi, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/649,632

(22) PCT Filed: Sep. 10, 2013

(86) PCT No.: PCT/JP2013/074368
§ 371 (c)(1),
(2) Date: Jun. 4, 2015

(87) PCT Pub. No.: WO2014/091806
PCT Pub. Date: Jun. 19, 2014

(65) Prior Publication Data
US 2015/0318933 A1    Nov. 5, 2015

(30) Foreign Application Priority Data

Dec. 11, 2012  (JP) .................................. 2012-269978

(51) Int. Cl.
*H04B 13/00*   (2006.01)
*H04B 5/00*    (2006.01)
(Continued)

(52) U.S. Cl.
CPC ......... *H04B 13/005* (2013.01); *H04B 5/0012* (2013.01); *A61B 5/0024* (2013.01); *A61B 5/0028* (2013.01); *A61B 5/02438* (2013.01)

(58) Field of Classification Search
None
See application file for complete search history.

(56) References Cited

U.S. PATENT DOCUMENTS 9,325,430 B2 *   4/2016  Ino ...................... A61B 5/0024
2005/0017841 A1 *  1/2005  Doi ....................... H04B 13/005
                                                       340/5.65

(Continued)

FOREIGN PATENT DOCUMENTS

CN         1866772 A      11/2006
CN       101635585 A       1/2010
(Continued)

*Primary Examiner* — Alejandro Rivero
(74) *Attorney, Agent, or Firm* — Wolf, Greenfield & Sacks, P.C.

(57) ABSTRACT

There is provided a communication terminal including an electrode unit configured to cause a dielectric to induce an electric field, and to transmit and receive signals via the dielectric, and a processing unit configured to obtain power from a reception signal received by the electrode unit, to process the reception signal, and to cause a response signal to be transmitted from the electrode unit through load modulation.

7 Claims, 10 Drawing Sheets

(51) Int. Cl.
*A61B 5/024* (2006.01)
*A61B 5/00* (2006.01)

(56) References Cited

U.S. PATENT DOCUMENTS

| | | | | |
|---|---|---|---|---|
| 2006/0281406 A1* | 12/2006 | Ishibashi | ............. | H04B 13/005 |
| | | | | 455/41.1 |
| 2009/0184842 A1* | 7/2009 | Baldus | ................. | G06F 19/323 |
| | | | | 340/870.07 |
| 2010/0019982 A1* | 1/2010 | Washiro | ................ | H01Q 1/273 |
| | | | | 343/860 |
| 2010/0045446 A1 | 2/2010 | Hyun et al. | | |
| 2012/0013446 A1* | 1/2012 | Ino | ...................... | A61B 5/0024 |
| | | | | 340/10.1 |
| 2012/0293118 A1* | 11/2012 | Kim | ....................... | H02J 5/005 |
| | | | | 320/108 |

FOREIGN PATENT DOCUMENTS

| | | |
|---|---|---|
| CN | 102340356 A | 2/2012 |
| EP | 1598965 A1 | 11/2005 |
| JP | 2005-352318 A | 12/2005 |
| JP | 2010-034617 A | 2/2010 |
| JP | 2011-199484 A | 10/2011 |
| JP | 2012-023565 A | 2/2012 |

\* cited by examiner

USING LOAD MODULATION FOR AUTHENTICATION VIA A DIELECTRIC MEDIUM, AND RELATED COMMUNICATION TERMINAL, COMMUNICATION DEVICE, COMMUNICATION METHOD AND COMMUNICATION SYSTEM

TECHNICAL FIELD

The present disclosure relates to a communication terminal, a communication device, a communication method, a program, and a communication system.

BACKGROUND ART

The technology for intra-body communication has been developed in which communication is established between devices via the human body. Examples of techniques that use both of intra-body communication and wireless communication which uses a communication technique supported, for example, by near field communication (NFC) include the technology described in Patent Literature 1.

CITATION LIST

Patent Literature

Patent Literature 1: JP 2005-352318A

SUMMARY OF INVENTION

Technical Problem

For example, the technology described in Patent Literature 1 uses both of intra-body communication and wireless communication (conventional wireless communication described in Patent Literature 1) that uses a communication technique, for example, supported by NFC. Accordingly, when the technology, for example, described in Patent Literature 1 is used, there is certainly possibility that processing in which intra-body communication is combined with wireless communication (conventional wireless communication described in Patent Literature 1) that uses a communication technique, for example, supported by NFC can improve the convenience of users.

Here, a device (portable device described in Patent Literature 1) to which the technology, for example, described in Patent Literature 1 is applied executes a reader/writer function to wirelessly communicate with an integrated circuit (IC) card. However, the reader/writer function does not work without a power supply. Consequently, a device to which the technology, for example, described in Patent Literature 1 is applied is not capable of performing wireless communication, for example, when there is no available power or the mounted battery runs out, etc.

Thus, even the use of the technology, for example, described in Patent Literature 1 does not necessarily allow the convenience of users to be improved.

The present disclosure provides a novel and improved communication terminal, communication device, communication method, program, and communication system that can improve the convenience of users through communication via a dielectric.

Solution to Problem

According to the present disclosure, there is provided a communication terminal including an electrode unit configured to cause a dielectric to induce an electric field, and to transmit and receive signals via the dielectric, and a processing unit configured to obtain power from a reception signal received by the electrode unit, to process the reception signal, and to cause a response signal to be transmitted from the electrode unit through load modulation.

According to the present disclosure, there is provided a communication device including an electrode unit configured to cause a dielectric to induce an electric field, and to transmit and receive signals via the dielectric, and a communication unit configured to cause a transmission signal to be transmitted from the electrode unit, and to process a response signal received by the electrode unit and transmitted through load modulation for the transmission signal.

According to the present disclosure, there is provided a communication method including a step of obtaining power from a reception signal received by an electrode unit, and processing the reception signal, the electrode unit causing a dielectric to induce an electric field, and transmitting and receiving signals via the dielectric, and a step of causing a response signal to be transmitted from the electrode unit through load modulation.

According to the present disclosure, there is provided a communication method including a step of causing a transmission signal to be transmitted from an electrode unit that causes a dielectric to induce an electric field, and transmits and receives signals via the dielectric, and a step of processing a response signal received by the electrode unit and transmitted through load modulation for the transmission signal.

According to the present disclosure, there is provided a program for causing a computer to execute a step of obtaining power from a reception signal received by an electrode unit, and processing the reception signal, the electrode unit causing a dielectric to induce an electric field, and transmitting and receiving signals via the dielectric, and a step of causing a response signal to be transmitted from the electrode unit through load modulation.

According to the present disclosure, there is provided a program for causing a computer to execute a step of causing a transmission signal to be transmitted from an electrode unit that causes a dielectric to induce an electric field, and transmits and receives signals via the dielectric, and a step of processing a response signal received by the electrode unit and transmitted through load modulation for the transmission signal.

According to the present disclosure, there is provided a communication system including a communication device, and a communication terminal configured to communicate with the communication device via a dielectric. The communication device includes a device side electrode unit configured to cause the dielectric to induce an electric field, and to transmit and receive signals via the dielectric, and a communication unit configured to cause a transmission signal to be transmitted from the device side electrode unit, and to process a response signal received by the device side electrode unit and transmitted through load modulation for the transmission signal. The communication terminal includes a terminal side electrode unit configured to cause the dielectric to induce an electric field, and to transmit and receive signals via the dielectric, and a processing unit configured to obtain power from a reception signal received by the terminal side electrode unit, to process the reception signal, and to cause the response signal to be transmitted from the terminal side electrode unit through load modulation.

Advantageous Effects of Invention

According to the present disclosure, it is possible to improve the convenience of users through communication via a dielectric.

DESCRIPTION OF EMBODIMENTS

Hereinafter, preferred embodiments of the present disclosure will be described in detail with reference to the appended drawings. Note that, in the present description and the drawings, elements that have substantially the same function and structure are denoted with the same reference signs, and repeated explanation is omitted.

The description will be now made in the following order.
1. Communication Method according to Present Embodiment
2. Communication System according to Present Embodiment
3. Program according to Present Embodiment (Communication Method according to Present Embodiment)

First of all, an example of a communication system according to the present embodiment will be described, and a communication method according to the present embodiment will be described before the description is made for the configurations of a communication terminal according to the present embodiment and a communication device according to the present embodiment, both of which are included in the communication system according to the present embodiment.

Figure 1:
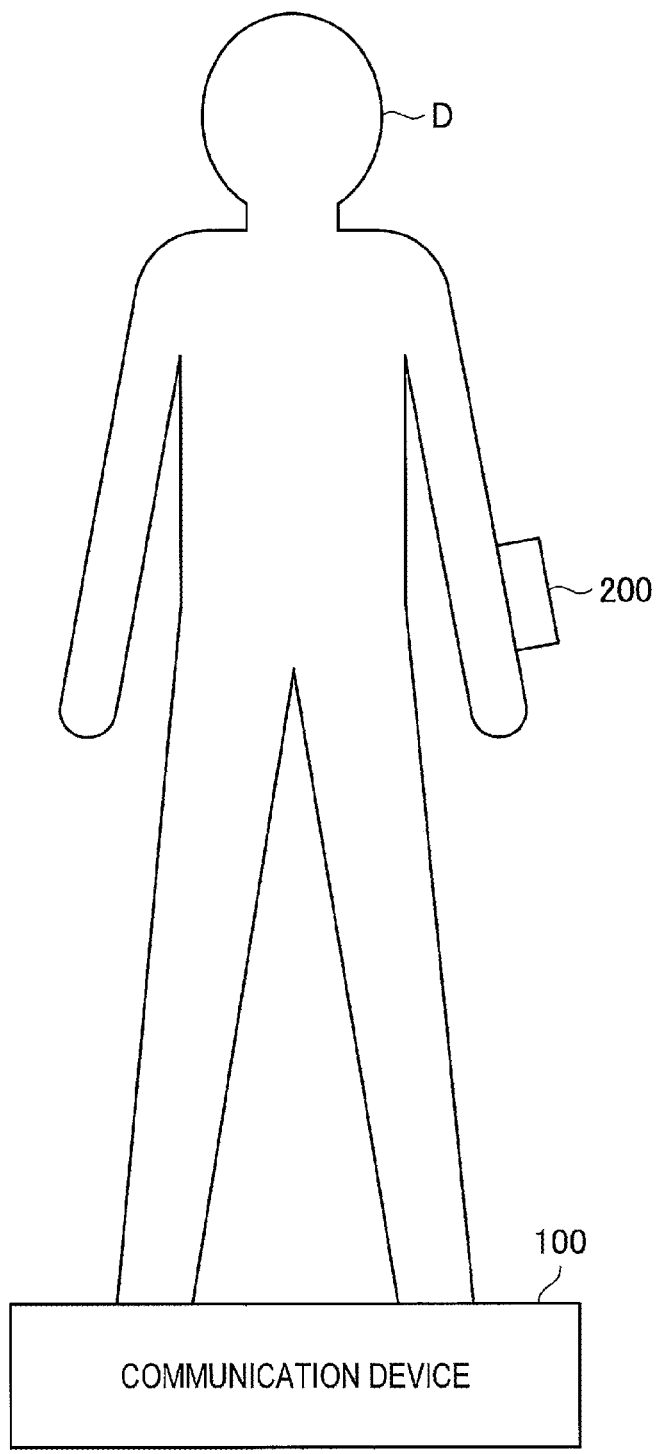
FIG. 1 is an explanatory diagram illustrating an example of a communication system according to the present embodiment.

FIG. 1 is an explanatory diagram illustrating an example of a communication system 1000 according to the present embodiment. The communication system 1000 includes, for example, a communication device 100 and a communication terminal 200.

The communication device 100 and the communication terminal 200 communicate with each other via a dielectric D. More specifically, a signal (voltage signal) is applied, for example, to a coupling electrode (discussed below) of the communication device 100 to polarize the dielectric D, and the dielectric D induces an electric field, so that the signal is transferred to a coupling electrode (discussed below) of the communication terminal 200 via the dielectric D in the communication system 1000. In addition, a signal (voltage signal) is applied, for example, for example, to the coupling electrode (discussed below) of the communication terminal 200 through load modulation to polarize the dielectric D, and the dielectric D induces an electric field, so that the signal is transferred to the coupling electrode (discussed below) of the communication device 100 via the dielectric D in the communication system 1000. The communication via the dielectric D according to the present embodiment will also be referred to as "dielectric communication" below.

Here, FIG. 1 illustrates a human body as the dielectric D, but the dielectric D according to the present embodiment is not limited to the human body. Examples of the dielectric D according to the present embodiment include resin, liquid, living bodies, ceramics, and polymers.

In addition, FIG. 1 illustrates an example in which the communication device 100 is positioned under the feet of a human body (example of the dielectric D, and the same applies hereinafter) and the communication terminal 200 is positioned at an arm of the human body, but the positions of the communication device 100 and the communication terminal 200 are not limited to the example illustrated in FIG. 1. The communication device 100 and the communication terminal 200 may be each positioned at any position at which the dielectric D can induce an electric field (position at which it is possible to perform dielectric communication).

The communication system 1000 as illustrated in FIG. 1 will be used as an example below to describe a communication method according to the present embodiment performed by the communication terminal 200 and a communication method according to the present embodiment performed by the communication device 100.

[1] Communication Method according to Present Embodiment Performed by Communication Terminal 200 according to Present Embodiment First of all, a communication method according to the present embodiment performed by the communication terminal 200 according to the present embodiment will be described.

The communication terminal 200 obtains power from a reception signal (signal corresponding to a transmission signal transmitted from the communication device 100) received by an electrode unit (discussed below) via the dielectric D, and processes the reception signal (signal processing). The communication terminal 200 then performs load modulation, for example, by using the obtained power, thereby transmitting a response signal from the electrode unit (discussed below) via the dielectric D (transmission processing). That is to say, the communication terminal 200 serves, for example, as a responder for NFC or the like in the communication system 1000.

The communication terminal 200 performs (1) signal processing and (2) transmission processing as a communication method according to the present embodiment.

Here, the communication terminal 200 is driven by power obtained from a reception signal received via the dielectric D, processes the reception signal, and transmits a response signal through load modulation. That is to say, the communication terminal 200 is capable of communicating with the communication device 100 via the dielectric D without any additional power supply or power supply circuit for dielectric communication in the communication system 1000 according to the present embodiment.

Accordingly, for example, even when the communication terminal 200 does not include any power supply, or when the communication terminal 200 does include a power supply but is not capable of obtaining power from the power supply because the power supply is off or the like, the communication terminal 200 can process a received reception signal and transmit a response signal via the dielectric D. That is to say, the use of the communication terminal 200 allows users of the communication terminal 200 to avoid such an inconvenient situation that the users are not able to enjoy a service (examples of the service will be discussed below) provided in the communication system 1000 because the communication terminal 200 fails to obtain power.

The communication terminal 200 can thus improve the convenience of users by performing the processing (signal processing) in (1) and the processing (transmission processing) in (2) as a communication method according to the present embodiment.

In addition, the communication terminal 200 can transmit a response signal via the dielectric D by performing load modulation on the basis of a processing result of a received reception signal, for example, even when a signal (signal indicating an instruction from a user) according to a user operation is not input.

[2] Communication Method according to Present Embodiment Performed by Communication Device 100 according to Present Embodiment Next, a communication method according to the present embodiment performed by the communication device 100 according to the present embodiment will be described.

The communication device 100 causes a transmission signal to be transmitted from an electrode unit (discussed below) (transmission processing), the electrode unit causing the dielectric D to induce an electric field, and transmitting and receiving signals via the dielectric D. In addition, the communication device 100 processes a response signal (signal processing) that has been transmitted through load modulation from the communication terminal 200 for the transmission signal. That is to say, the communication device 100 serves, for example, as a reader/writer (or interrogator) for NFC or the like in the communication system 1000.

The communication device 100 performs (I) transmission processing and (II) signal processing as a communication method according to the present embodiment.

As discussed above, the communication terminal 200 is driven by power obtained from a transmission signal transmitted by the communication device 100 in the processing (transmission processing) in (I), and transmits a response signal for the transmission signal in the communication system 1000. In addition, the communication device 100 processes, in the processing (signal processing) in (II), the response signal transmitted from the communication terminal 200 through load modulation. That is to say, users of the communication terminal 200 can avoid such an inconvenient situation that the users are not able to enjoy a service (examples of the service will be discussed below as a use case by the communication system 1000) provided in the communication system 1000 because the communication terminal 200 fails to obtain power in the communication system 1000 including the communication device 100 and the communication terminal 200.

Thus, a communication system is implemented in which the communication device 100 can improve the convenience of users through communication via the dielectric D by performing the processing (transmission processing) in (I) and the processing (signal processing) in (II) as a communication method according to the present embodiment.

(Communication System according to Present Embodiment)

Next, an example of the configuration of the communication terminal 100 that allows the communication device according to the present embodiment to perform a communication method, and an example of the configuration of the communication terminal 200 that allows the communication terminal according to the present embodiment to perform a communication method will be each described. Additionally, a use case by the communication system 1000 which can be implemented by application of a communication method according to the present embodiment will also be described below.

[I] Configuration of Communication Device 100 according to Present Embodiment

Figure 2:
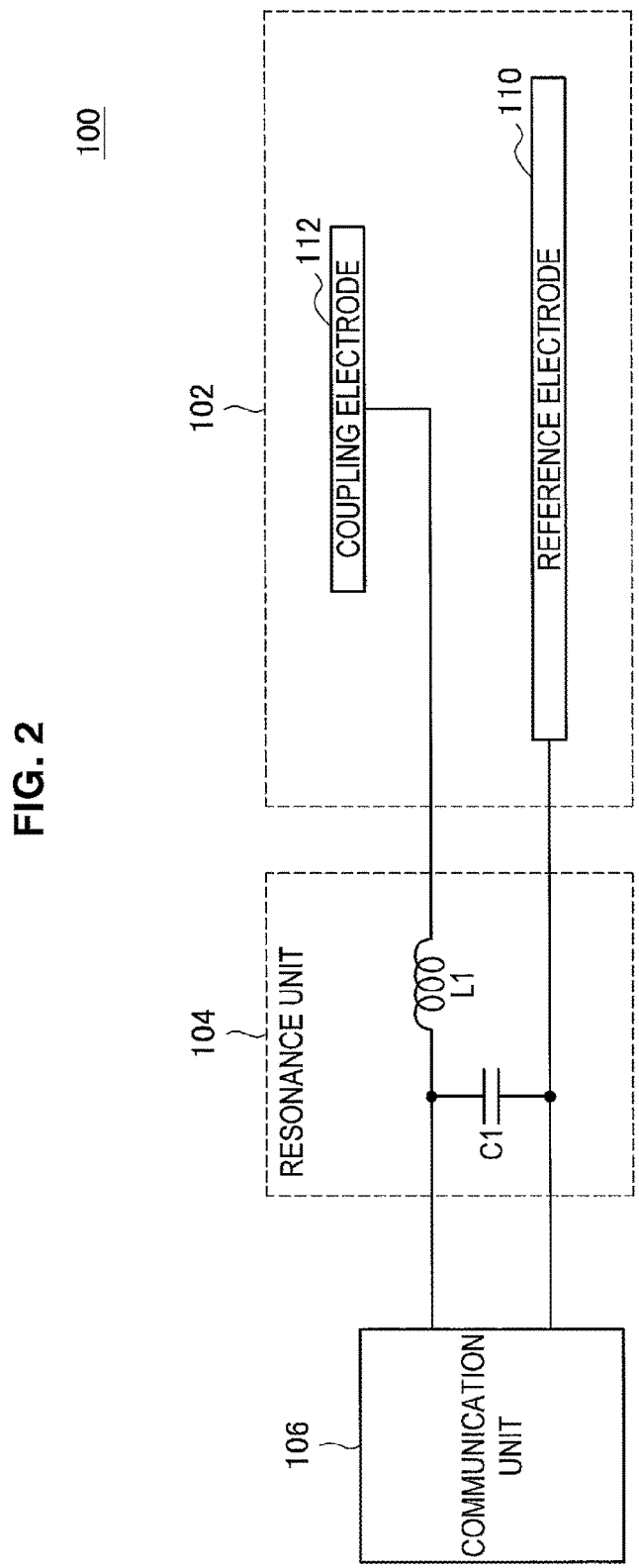
FIG. 2 is an explanatory diagram illustrating an example of a configuration of a communication device according to the present embodiment.

FIG. 2 is an explanatory diagram illustrating an example of the configuration of the communication device 100 according to the present embodiment.

The communication device 100 includes, for example, an electrode unit 102 (device side electrode unit), a resonance unit 104, and a communication unit 106.

In addition, the communication device 100 may include, for example, read only memory (ROM) (not illustrated), random access memory (RAM) (not illustrated), a control unit (not illustrated), a storage unit (not illustrated), an operation unit (not illustrated) that a user can operate, a display unit (not illustrated) that displays a variety of screens on a display screen, and the like. The communication device 100 connects the respective structural elements, for example, using a bus as a transmission path of data.

Here, the control unit (not illustrated) includes, for example, a micro processing unit (MPU), a variety of processing circuits and the like, and controls the whole of the communication device 100. In addition, the control unit (not illustrated) may serve, for example, as the communication unit 106.

The ROM (not illustrated) stores control data such as a program and an operation parameter used by the control unit (not illustrated). The RAM (not illustrated) temporarily stores a program and the like executed by the control unit (not illustrated).

The storage unit (not illustrated) is a storage medium included in the communication device 100, and stores, for example, various types of data such as applications. Here, examples of the storage unit (not illustrated) include a magnetic recording medium such as a hard disk, and non-volatile memory such as flash memory. In addition, the storage unit (not illustrated) may be detachably attached to the communication device 100.

Examples of the operation unit (not illustrated) include a button, a direction key, a rotary selector such as a jog dial, or a combination thereof. Furthermore, the communication device 100 may be connectable, for example, to an operation input device (such as a keyboard and a mouse) used as an external device of the communication device 100.

The display unit (not illustrated) is a display means included in the communication device 100, and displays various types of information (such as images and/or letters) on a display screen. Examples of screens displayed on the display screen of the display unit (not illustrated) include an operation screen for causing the communication device 100 to perform a desired operation, and a screen on which a message is displayed for a user of the communication device 100.

Here, examples of the display unit (not illustrated) include a display device such as a liquid crystal display and an organic electro-luminescence (EL) display which is also referred to as organic light emitting diode (OLED) display. In addition, the communication device 100 can include, for example, a touch screen for the display unit (not illustrated). In that case, the display unit (not illustrated) functions as an operation display unit that is capable of both user operation and display.

The electrode unit 102 causes the dielectric D to induce an electric field, and transmits and receives signals via the dielectric D. The electric unit 102 includes, for example, a reference electrode 110 and a coupling electrode 112.

The reference electrode 110 serves as a ground (reference potential point) in the electrode unit 102. Examples of the reference electrode 110 include a metal plate, a conductive mat, and a conductive sheet each of which has a larger area than the coupling electrode 112.

The coupling electrode 112 transmits and receives signals via the dielectric D in the electrode unit 102, including transmitting a transmission signal and receiving a response signal via the dielectric D, etc. Examples of the coupling electrode 112 include a metal plate having a smaller area than the reference electrode 110, a conductive mat having a smaller area than the reference electrode 110, and a conductive sheet having a smaller area than the reference electrode 110. In addition, the coupling electrode 112 is provided, for example, at a position at which electrostatic coupling is stronger with the dielectric D than the reference electrode 110.

The resonance unit 104 resonates signals at a predetermined frequency, the signals being transmitted and received by the electrode unit 102. FIG. 2 illustrates an example in which the resonance unit 104 includes, for example, a resonance circuit that includes an inductor L1 having inductance and a capacitor C1 having predetermined capacitance, and performs impedance conversion. Examples of the predetermined frequency (resonance frequency) at which the resonance unit 104 resonates signals include a frequency of 13.56 [MHz], which is the frequency of signals transmitted and received by the electrode unit 102.

Additionally, the configuration of the resonance unit 104 is not limited to the configuration illustrated in FIG. 2. For example, the resonance unit 104 may include any resonance circuit that can resonate signals at a predetermined frequency, the signals being transmitted and received by the electrode unit 102. In addition, the resonance unit 104 may also include a circuit such as a transformer capable of performing impedance conversion.

The communication unit 106 plays a leading role for performing the processing (transmission processing) in (I) and the processing (signal processing) in (II) for a communication method according to the present embodiment. More specifically, the communication unit 106, for example, causes a transmission signal to be transmitted from the electrode unit 102, and processes a response signal received by the electrode unit 102 and transmitted through load modulation for the transmission signal.

Figure 3:
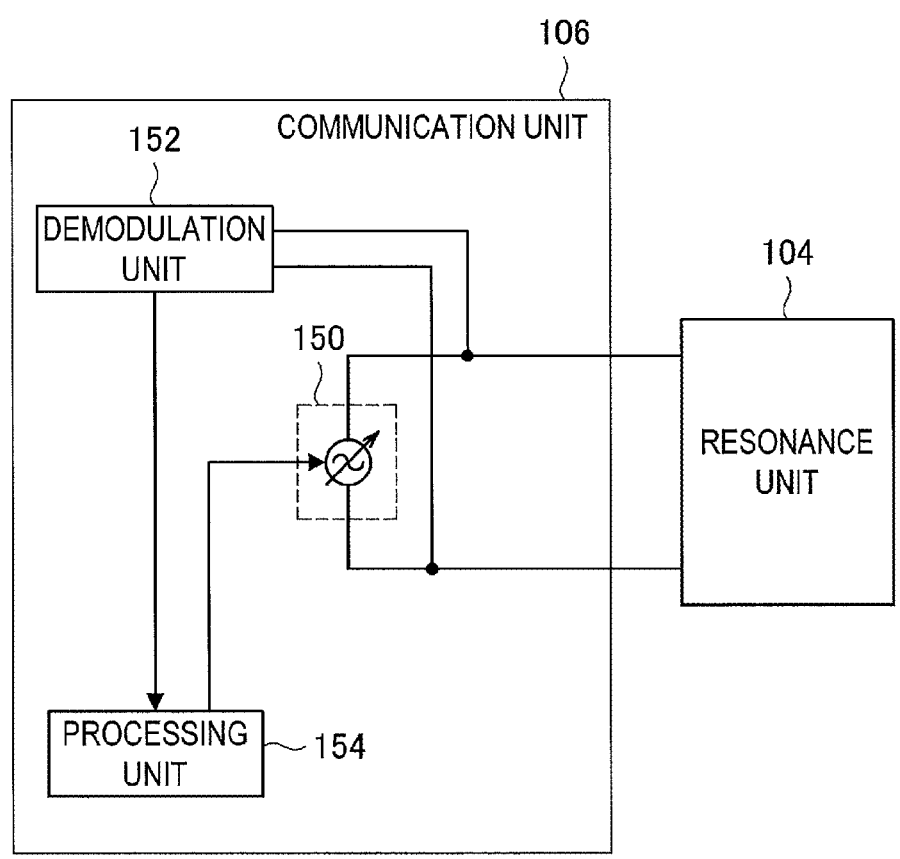
FIG. 3 is an explanatory diagram illustrating an example of a configuration of a communication unit included in the communication device according to the present embodiment.

FIG. 3 is an explanatory diagram illustrating an example of the configuration of the communication unit 106 included in the communication device 100 according to the present embodiment. Here, FIG. 3 also illustrates a resonance unit 104.

The communication unit 106 includes, for example, a signal generating unit 150, a demodulation unit 152, and a processing unit 154, and serves as a reader/writer (or interrogator) for NFC or the like. In addition, the communication unit 106 may further include, for example, an encoding circuit (not illustrated), an anti-collision circuit, and the like.

Figure 4:
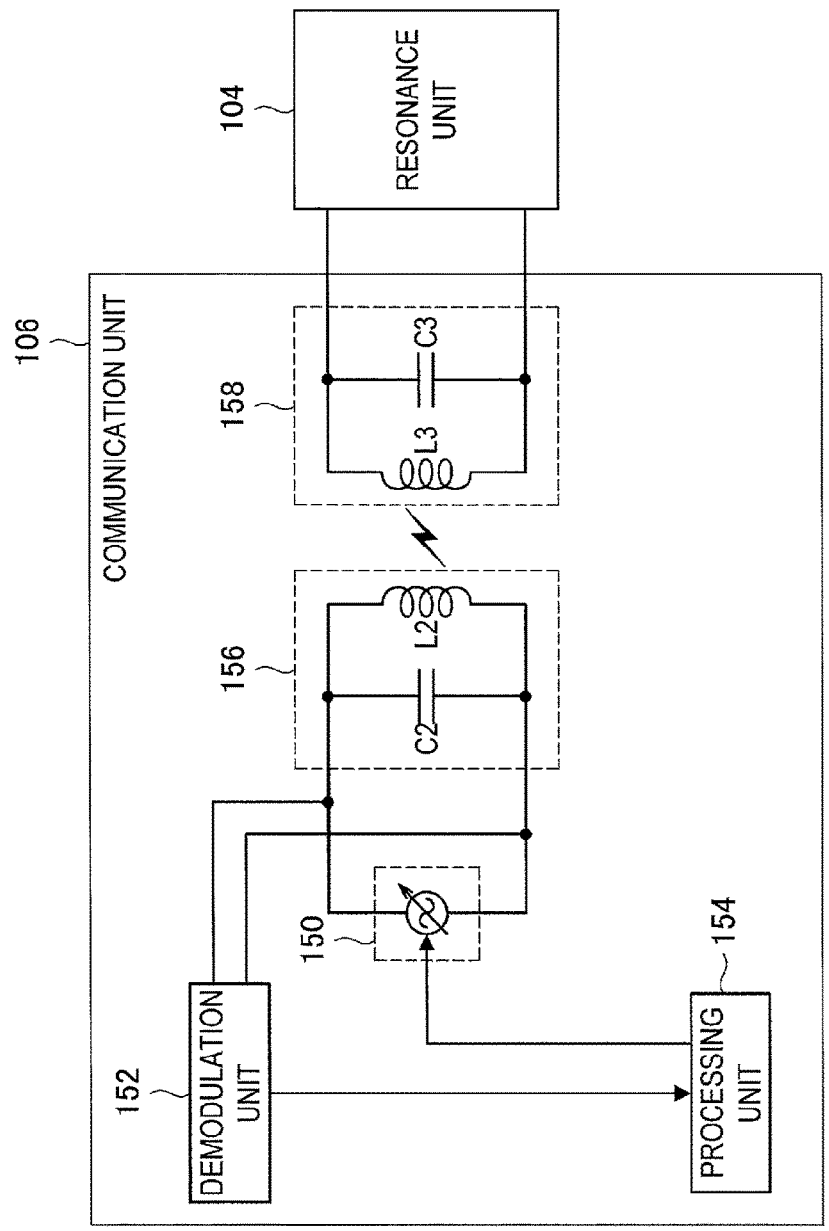
FIG. 4 is an explanatory diagram illustrating another example of the communication unit included in the communication device according to the present embodiment.

The signal generating unit 150 receives a signal generating instruction transferred, for example, from the processing unit 154, and generates a signal (signal corresponding to a transmission signal according to the present embodiment) according to the signal generating instruction. In addition, the signal generating unit 150 receives a signal transmission stop instruction indicating a transmission stop of a signal, and stops the generation of a signal, the signal transmission stop instruction being transferred, for example, from the processing unit 154. Here, FIG. 4 illustrates an alternating-current power supply as the signal generating unit 150, but the configuration of the signal generating unit 150 according to the present embodiment is not limited thereto. For example, the signal generating unit 150 according to the present embodiment can include a modulation circuit (not illustrated) that performs amplitude shift keying (ASK) modulation and an amplifier circuit (not illustrated) that amplifies an output of the modulation circuit.

Here, examples of signals generated by the signal generating unit 150 include a signal including an identification information transmission request (example of an instruction) for requesting transmission of identification information, and a signal including a variety of processing instructions to an external device and data to be processed.

Identification information according to the present embodiment is information (data) that can be used for identifying an external device such as the communication terminal 200, which performs communication via the dielectric D. Examples of identification information according to the present embodiment include data indicating the identification number unique to an external device, data indicating international mobile subscriber identity (IMSI), data indicating the type of external device (such as a maker and a model), and electric power waveform data indicating an electric power waveform while an external device is in use (external device has been driven). Additionally, identification information according to the present embodiment is not limited the above-described examples as long as the identification information is information that can be used for identifying an external device.

Additionally, signals generated by the signal generating unit 150 are not limited thereto. For example, a signal according to the present embodiment may be a signal (such as an unmodulated signal) that serves to supply power to an external device such as the communication terminal 200, which performs communication via the dielectric D.

The demodulation unit 152 detects, for example, the envelope of an amplitude change in voltage between the signal generating unit 150 and the resonance unit 104, and binarizes the detected signals to demodulate a response signal received by the electrode unit 102. The demodulation unit 152 then transfers the demodulated response signal to the processing unit 154. Additionally, means of the demodulation unit 152 to demodulate a response signal is not limited thereto, but, for example, the demodulation unit 152 can also demodulate a response signal by using a phase change in voltage between the signal generating unit 150 and the resonance unit 104.

The processing unit 154 includes, for example, a MPU and the like, and processes a response signal transferred from the demodulation unit 152. Examples of processing by the processing unit 154 (examples of processing by the communication unit 106) will be described in the following use case by the communication system 1000.

The communication unit 106 according to the present embodiment is, for example, configured as illustrated in FIG. 3 to cause a transmission signal to be transmitted from the electrode unit 102, and to process a response signal received by the electrode unit 102.

Additionally, the configuration of the communication unit 106 according to the present embodiment is not limited to the configuration illustrated in FIG. 3. FIG. 4 is an explanatory diagram illustrating another example of the communication unit 106 included in the communication device 100 according to the present embodiment. Here, as in FIG. 3, FIG. 4 also illustrates a resonance unit 104.

The communication unit 106 according to the other example includes a signal generating unit 150, a demodulation unit 152, a processing unit 154, a first carrier wave transmitting and receiving unit 156, and a second carrier wave transmitting and receiving unit 158. In addition, the communication unit 106 according to the other example may further include, for example, an encoding circuit (not illustrated), an anti-collision circuit, and the like.

The signal generating unit 150 generates a signal according to a signal generating instruction, and stops the generation of a signal in accordance with a signal transmission stop instruction in the same way as the signal generating unit 150 illustrated in FIG. 3.

The demodulation unit 152 detects the envelope of an amplitude change in voltage at an end of an antenna of the first carrier wave transmitting and receiving unit 156 discussed below, and binarizes the detected signals to demodulate a response signal received by the electrode unit 102. Additionally, means of the demodulation unit 152 to demodulate a response signal is not limited thereto, but, for example, the demodulation unit 152 can also demodulate a response signal by using a phase change in voltage at an end of an antenna of the first carrier wave transmitting and receiving unit 156.

The first carrier wave transmitting and receiving unit 156 includes, for example, an inductor L2 having predetermined inductance and a capacitor C2 having predetermined capacitance, and is included in a resonance circuit. Examples of a resonance frequency of the first carrier wave transmitting and receiving unit 156 include a resonance frequency of 13.56 [MHz]. The first carrier wave transmitting and receiving unit 156 is configured as described above to transmit a signal generated by the signal generating unit 150, and to receive a response signal received by the electrode unit 102. That is to say, the first carrier wave transmitting and receiving unit 156 serves as a first communication antenna of the communication unit 106.

The second carrier wave transmitting and receiving unit 158 includes, for example, an inductor L3 having predetermined inductance and a capacitor C3 having predetermined capacitance, and is included in a resonance circuit. Examples of a resonance frequency of the second carrier wave transmitting and receiving unit 158 include a resonance frequency of 13.56 [MHz]. The second carrier wave transmitting and receiving unit 158 is configured as described above to receive a signal transmitted from the first carrier wave transmitting and receiving unit 156, and to transmit a response signal received by the electrode unit 102. That is to say, the second carrier wave transmitting and receiving unit 158 serves as a second communication antenna of the communication unit 106.

Even configured as illustrated in FIG. 4, the communication unit 106 according to the present embodiment causes a transmission signal to be transmitted from the electrode unit 102, and processes a response signal received by the electrode unit 102 as in the configuration illustrated in FIG. 3.

The communication device 100 is, for example, configured as illustrated in FIG. 2 to perform the processing (transmission processing) in (I) and the processing (signal processing) in (II) for a communication method according to the present embodiment. Thus, a communication system is implemented in which, for example, the configuration of the communication device 100 as illustrated in FIG. 2 allows the convenience of users to be improved through communication via the dielectric D.

Additionally, the configuration of the communication device 100 according to the present embodiment is not limited to the configuration illustrated in FIG. 2.

For example, the communication device 100 can also be configured without any resonance unit 104. The communication device 100 can cause transmit a transmission signal to be transmitted from the electrode unit 102 and process a response signal received by the electrode unit 102 even without the resonance unit 104. Accordingly, even when the communication device 100 does not include the resonance unit 104, it is possible to implement a communication system in which it is possible to improve the convenience of users through communication via the dielectric D.

Figure 5:
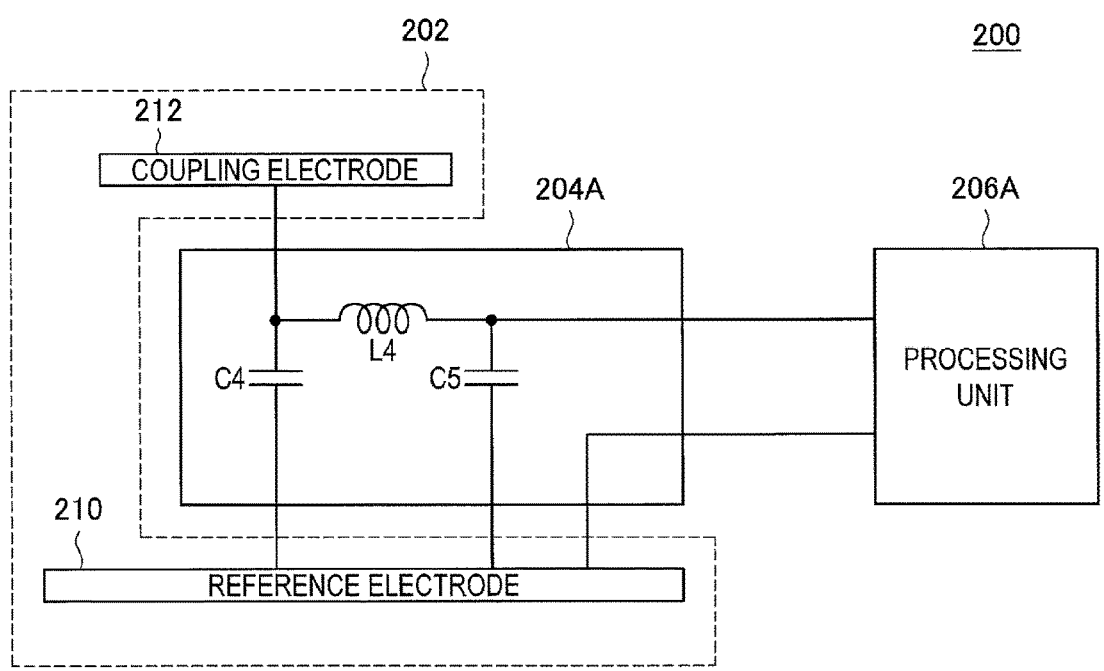
FIG. 5 is an explanatory diagram illustrating an example of a configuration of a communication terminal according to the present embodiment.

[II] Configuration of Communication Terminal 200 according to Present Embodiment FIG. 5 is an explanatory diagram illustrating an example of the configuration of the communication terminal 200 according to the present embodiment.

The communication terminal 200 includes, for example, an electrode unit 202 (terminal side electrode unit), a resonance unit 204A, and a processing unit 206A.

In addition, the communication terminal 200 may include, for example, ROM (not illustrated), RAM (not illustrated), a control unit (not illustrated), a storage unit (not illustrated), an operation unit (not illustrated) that a user can operate, a display unit (not illustrated) that displays a variety of screens on a display screen. The communication terminal 200 connects the respective structural elements, for example, using a bus as a transmission path of data.

Here, the control unit (not illustrated) includes, for example, an MPU, a variety of processing circuits and the like, and controls the whole of the communication terminal 200. In addition, the control unit (not illustrated) may serve, for example, as the processing unit 206A.

The ROM (not illustrated) stores control data such as a program and an operation parameter used by the control unit (not illustrated). The RAM (not illustrated) temporarily stores a program and the like executed by the control unit (not illustrated).

The storage unit (not illustrated) is a storage means included in the communication terminal 200, and stores various types of data such as applications. Here, examples of the storage unit (not illustrated) include a magnetic recording medium such as a hard disk, and nonvolatile memory such as flash memory. In addition, the storage unit (not illustrated) may be detachably attached to the communication terminal 200.

Examples of the operation unit (not illustrated) include a button, a direction key, a rotary selector such as a jog dial, or a combination thereof. Furthermore, the communication terminal 200 may be connectable, for example, to an operation input device (such as a keyboard and a mouse) used as an external device of the communication terminal 200.

The display unit (not illustrated) is a display means included in the communication terminal 200, and displays various types of information (such as images and/or letters) on a display screen. Examples of screens displayed on the display screen of the display unit (not illustrated) include an operation screen for causing the communication terminal 200 to perform a desired operation, and a screen on which a message is displayed for a user of the communication terminal 200.

Here, examples of the display unit (not illustrated) include a display device such as a liquid crystal display and an organic EL display. In addition, the communication terminal 200 may include, for example, a touch screen for the display unit (not illustrated). In that case, the display unit (not illustrated) functions as an operation display unit that is capable of both user operation and display.

The electrode unit 202 causes the dielectric D to induce an electric field, and transmits and receives signals via the dielectric D. The electrode unit 202 includes, for example, a reference electrode 210 and a coupling electrode 212.

The reference electrode 210 serves as a ground in the electrode unit 202. Examples of the reference electrode 210 include a metal plate having a larger area than the coupling electrode 212.

The coupling electrode 212 transmits and receives signals via the dielectric D in the electrode unit 202, including receiving a reception signal and transmitting a response signal via the dielectric D, etc. Examples of the coupling electrode 212 include a metal plate having a smaller area than the reference electrode 210. In addition, the coupling electrode 212 is provided, for example, at a position at which electrostatic coupling is stronger with the dielectric D than the reference electrode 210.

The resonance unit 204A resonates signals at a predetermined frequency, the signals being transmitted and received by the electrode unit 202. FIG. 5 illustrates an example in which the resonance unit 204A includes, for example, a resonance circuit (first resonance circuit) that includes an inductor L4 having predetermined inductance and capacitors C4 and C5 each having predetermined capacitance, and performs impedance conversion. Examples of the predetermined frequency (resonance frequency) at which the resonance unit 204A resonates signals include a frequency of 13.56 [MHz], which is a frequency of signals transmitted and received by the electrode unit 202.

Additionally, the configuration of the resonance unit 204A is not limited to the configuration illustrated in FIG. 5. For example, the resonance unit 204A may include any resonance circuit that can resonate signals at a predetermined frequency, the signals being transmitted and received by the electrode unit 202. In addition, the resonance unit 204A may also include a circuit such as a transformer capable of performing impedance conversion.

The processing unit 206A serves to perform the processing (signal processing) in (1) and the processing (transmission processing) in (2) for a communication method according to the present embodiment. More specifically, the processing unit 206A is driven, for example, by power obtained from a reception signal received via the dielectric D, processes the reception signal, and causes a response signal to be transmitted from the electrode unit 202 through load modulation.

Figure 6:
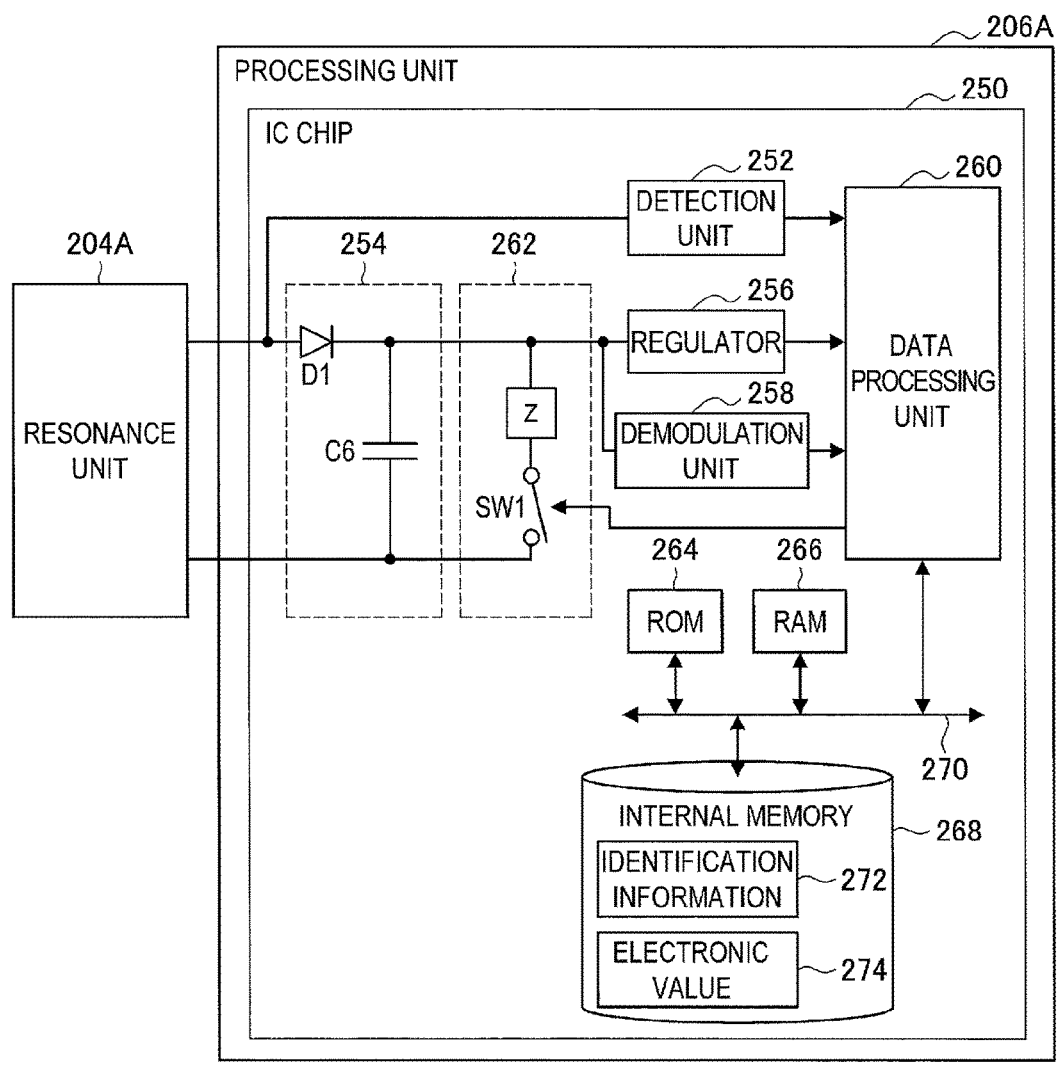
FIG. 6 is an explanatory diagram illustrating an example of a configuration of a processing unit included in the communication terminal according to the present embodiment.

FIG. 6 is an explanatory diagram illustrating an example of the configuration of the processing unit 206A included in the communication terminal 200 according to the present embodiment. Here, FIG. 6 also illustrates a resonance unit 204A. In addition, FIG. 6 illustrates that the processing unit 206A includes an IC chip 250 that demodulates and processes a reception signal received by the electrode unit 202, and to causes a response signal to be transmitted through load modulation. Additionally, the processing unit 206A according to the present embodiment does not necessarily have to include each structural element included in the IC chip 250 illustrated in FIG. 6 in a form of an IC chip.

The IC chip 250 includes, for example, a detection unit 252, a wave detecting unit 254, a regulator 256, a demodulation unit 258, a data processing unit 260, and a load modulation unit 262. Additionally, although not illustrated in FIG. 6, the IC chip 250 may further include, for example, a protective circuit (not illustrated) that prevents overvoltage and overcurrent from being applied to the data processing unit 260. Here, examples of the protective circuit (not illustrated) include a clamping circuit including a diode and the like.

In addition, the IC chip 250 includes, for example, ROM 264, RAM 266, and an internal memory 268. The data processing unit 260, the ROM 264, the RAM 266, and the internal memory 268 are connected to each other, for example, by a bus 270 used as a transmission path of data.

The carrier detection unit 252 generates, for example, a rectangular detection signal on the basis of a signal transferred from the resonance unit 204A, and transfers the detection signal to the data processing unit 260. In addition, the data processing unit 260 uses the transferred detection signal, for example, as a processing clock for data processing. Here, the detection signal is based on a signal transferred from the resonance unit 204A, so that the detection signal synchronizes with the frequency of a reception signal received by the electrode unit 202. Thus, with the carrier detection unit 252, the IC chip 250 can perform processing with the communication device 100, which perform communication via the dielectric D, in synchronization with the communication device 100.

The wave detecting unit 256 rectifies a signal (voltage signal) transferred from the resonance unit 204A. Here, the wave detecting unit 256 includes, for example, a diode D1 and a capacitor C6.

The regulator 256 smoothes signals transferred from the resonance unit 204A, stabilizes the voltage of the signals, and outputs drive voltage to the data processing unit 260. Here, the regulator 256 uses, for example, a direct-current component of a signal transferred from the resonance unit 204A as drive voltage.

The demodulation unit 258 demodulates a reception signal on the basis of a signal received from the resonance unit 204A, and outputs data (such as data signals having values binarized into a high level and a low level) corresponding to the reception signal. Here, the demodulation unit 258 outputs, for example, an alternating-current component of a signal transferred from the resonance unit 204A as data.

The data processing unit 260 is driven by using, for example, drive voltage output from the regulator 256 as a power supply, and processes data demodulated by the demodulation unit 258. Here, the data processing unit 260 includes, for example, an MPU, a variety of processing circuits, and the like.

In addition, the data processing unit 260 selectively generates control signals (such as high level/low level signals) in accordance with a processing result, the control signals controlling load modulation for the transmission of a response signal. The data processing unit 260 then selectively outputs the control signals to the load modulation unit 262.

The data processing unit 260 outputs a control signal to the load modulation unit 262, so that the load modulation unit 262 performs load modulation and a signal according to the modulation is transferred to the resonance unit 204A. That is to say, a control signal output by the data processing unit 260 corresponds to a signal for controlling the transmission of a response signal. Here, examples of control signals generated by the data processing unit 260 include a signal including a processing result according to an instruction (request) included in a reception signal, a signal including data (example of information according to an instruction (request) included in a reception signal) such as identification information stored in the internal memory 268, and a signal including the processing result and the stored data.

In addition, the data processing unit 260 reads out and updates data stored in the internal memory 268, for example, on the basis of an instruction included in data demodulated by the demodulation unit 258.

The load modulation unit 262 includes, for example, a load Z and a switch SW1, and perform load modulation by selectively connecting (enabling) the load Z in accordance with a signal level (such as a high level/low level) of a control signal transferred from the data processing unit 260. Here, the load Z includes, for example, a resistance having a predetermined resistance value, but the load Z is not limited thereto. Meanwhile, the switch SW1 includes, for example, a p-channel metal oxide semiconductor field effect transistor (MOSFET) and an n-channel MOSFET, but the switch SW1 is not limited to thereto.

The ROM 264 stores control data such as a program and an operation parameter used by the data processing unit 260. The RAM 266 temporarily stores control a program executed by the data processing unit 260, a result of an operation, an execution state, and the like.

The internal memory 268 is a storage means included in the IC chip 250 and has, for example, tamper resistance, while the data processing unit 260, for example, reads out data, newly writes data, and updates data. The internal memory 268 stores, for example, identification information, electronic values, key data used for encoding, and various types of data such as applications. Here, FIG. 6 illustrates an example in which the internal memory 268 stores identification information 272 and an electronic value 274, but data stored in the internal memory 268 is not limited thereto.

The IC chip 250 is, for example, configured as illustrated in FIG. 6 to be driven by power obtained from a reception signal (signal transferred from the resonance unit 204A in the example of FIG. 6) received by the electrode unit 202, to process the reception signal, and to transmit a response signal through load modulation. Additionally, it is needless to say that the configuration of the IC chip 250 according to the present embodiment is not limited to the configuration illustrated in FIG. 6.

The processing unit 206A is, for example, configured as illustrated in FIG. 6 to be driven by power obtained from a reception signal received by the electrode unit 202 via the dielectric D, to process the reception signal, and to cause a response signal to be transmitted from the electrode unit 202 through load modulation.

The communication terminal 200 is, for example, configured as illustrated in FIG. 5 to perform the processing (signal processing) in (1) and the processing (transmission processing) in (2) for a communication method according to the present embodiment. The communication terminal 200 can, thus, improve the convenience of users.

Additionally, the configuration of the communication terminal 200 according to the present embodiment is not limited to the configuration illustrated in FIG. 5.

Figure 7:
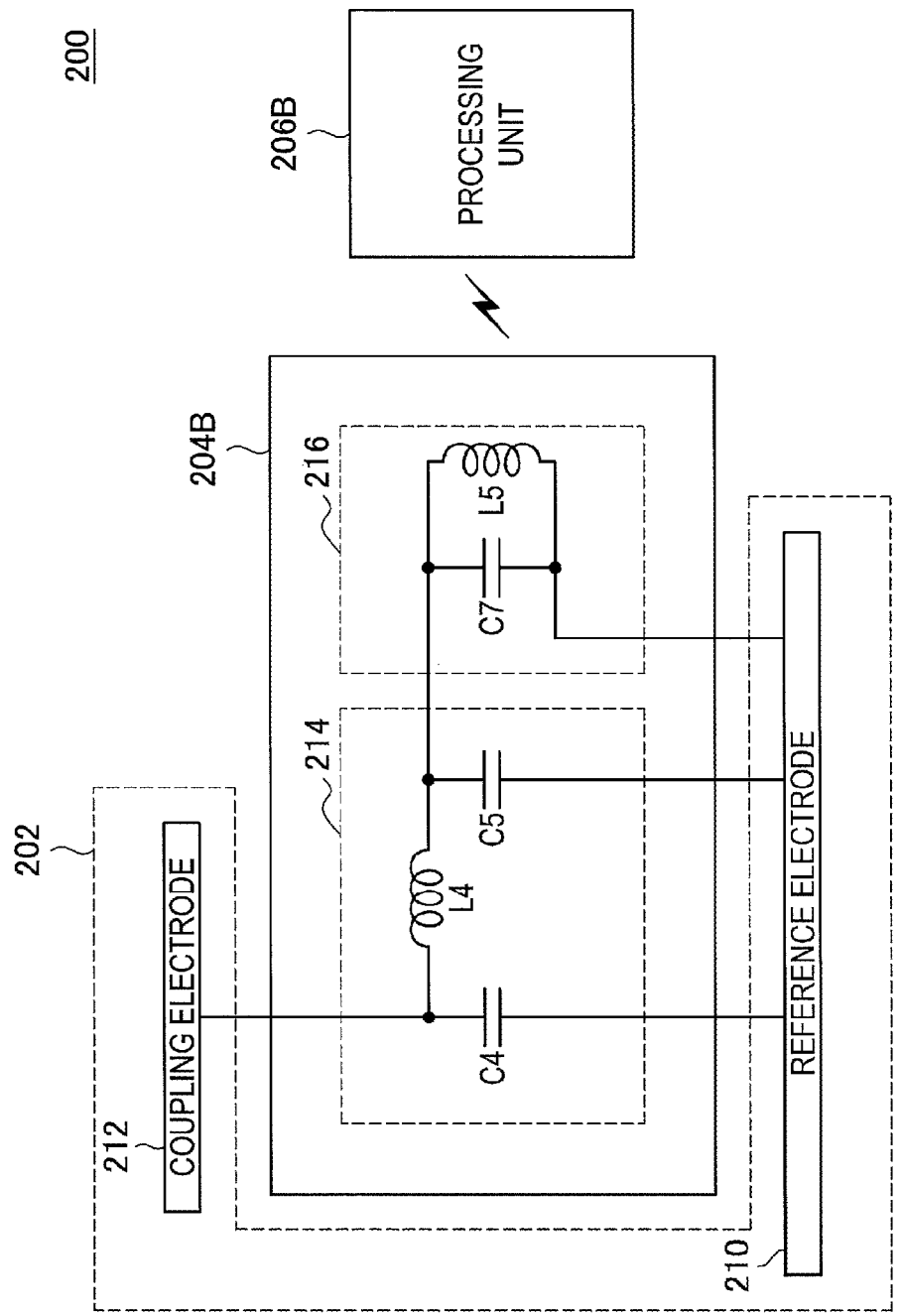
FIG. 7 is an explanatory diagram illustrating another example of the configuration of the communication terminal according to the present embodiment.

FIG. 7 is an explanatory diagram illustrating another example of the configuration of the communication terminal 200 according to the present embodiment.

The communication terminal 200 according to the other example includes, for example, an electrode unit 202 (terminal side electrode unit), a resonance unit 204B, and a processing unit 206B.

In addition, the communication terminal 200 according to the other example may include, for example, ROM (not illustrated), RAM (not illustrated), a control unit (not illustrated), a storage unit (not illustrated), an operation unit (not illustrated) that a user can operate, a display unit (not illustrated) that displays a variety of screens on a display screen, and the like. The communication terminal 200 connects the respective structural elements, for example, using a bus as a transmission path of data.

The resonance unit 204B resonates signals at a predetermined frequency, the signals being transmitted and received by the electrode unit 202. The resonance unit 204B includes, for example, a first resonance circuit 214 and a second resonance circuit 216.

The first resonance circuit 214 is configured in the same way as the resonance unit 204A illustrated in FIG. 5, and performs impedance conversion.

The second resonance circuit 216 is electrically connected to the first resonance circuit 214, and has an inductor L5 connected to a condenser C7 in parallel, the inductor L5 having predetermined inductance, the condenser C7 having predetermined capacitance. Examples of the predetermined frequency (resonance frequency) at which the second resonance circuit 216 resonates signals include a frequency of 13.56 [MHz], which is a frequency of signals transmitted and received by the electrode unit 202.

The second resonance circuit 216 is configured as described above to transmit a reception signal received by the electrode unit 202, and to receive a response signal transmitted from the processing unit 206 discussed below. That is to say, the second resonance circuit 216 serves as a communication antenna of the resonance unit 204B.

The resonance unit 204B includes, for example, a first resonance circuit 214 and a second resonance circuit 216 as described above. Additionally, the configuration of the resonance unit 204B is not limited to the configuration illustrated in FIG. 6. For example, the first resonance circuit included in the resonance unit 204B may also include a circuit such as a transformer capable of performing impedance conversion.

The processing unit 206B serves to perform the processing (signal processing) in (1) and the processing (transmission processing) in (2) for a communication method according to the present embodiment. More specifically, the processing unit 206B is driven, for example, by power obtained from a reception signal received via the dielectric D, processes the reception signal, and causes a response signal to be transmitted from the electrode unit 202 through load modulation.

Figure 8:
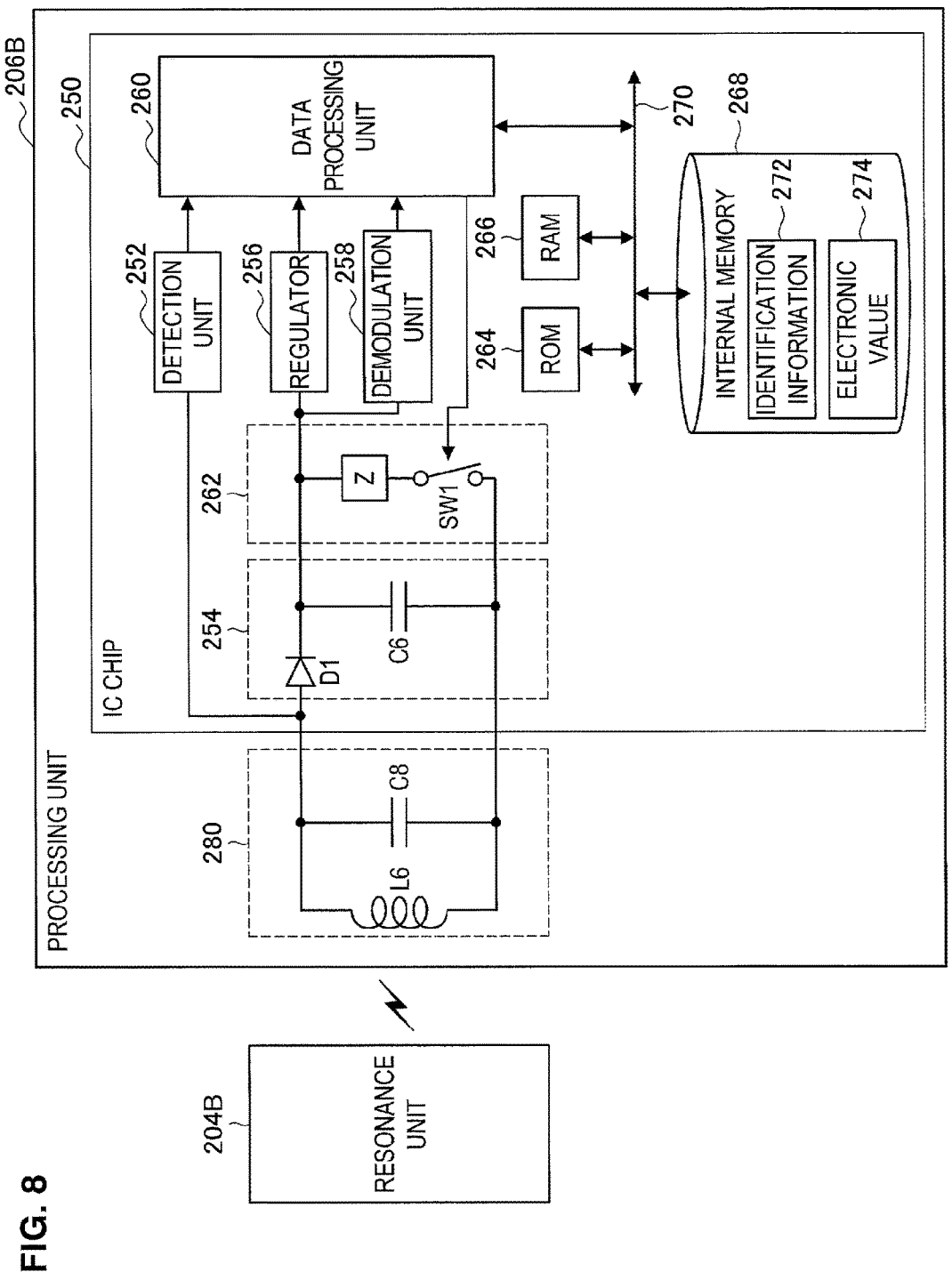
FIG. 8 is an explanatory diagram illustrating an example of the configuration of the processing unit included in the communication terminal according to the present embodiment.

FIG. 8 is an explanatory diagram illustrating an example of the configuration of the processing unit 206B included in the communication terminal 200 according to the present embodiment. Here, FIG. 8 also illustrates a resonance unit 204B. In addition, FIG. 8 illustrates that the processing unit 206B includes an IC chip 250 which demodulates and processes a reception signal received by the electrode unit 202, and causes a response signal to be transmitted through load modulation. Additionally, the processing unit 206B according to the present embodiment does not necessarily have to include each structural element included in the IC chip 250 illustrated in FIG. 8 in a form of an IC chip.

The processing unit 206B includes a resonance circuit 280 and an IC chip 250.

The resonance circuit 280 has an inductor L6 connected to a condenser C8 in parallel, the inductor L6 having predetermined inductance, the condenser C8 having predetermined capacitance. Examples of the predetermined frequency (resonance frequency) at which the resonance circuit 280 resonates signals include a frequency of 13.56 [MHz], which is a frequency of signals transmitted and received by the electrode unit 202.

The resonance circuit 280 is configured as described above to receive a reception signal transmitted from the second resonance circuit 216 of the resonance unit 204B, and to transmit a response signal transferred from the IC chip 250. More specifically, the resonance circuit 280 produces induced voltage through electromagnetic induction in response to the reception of a reception signal, and outputs reception voltage obtained by resonating the induced voltage at a predetermined resonance frequency to the IC chip 250. In addition, the resonance circuit 280 transmits a response signal through load modulation performed by the load modulation unit 264 included in the IC chip 250. That is to say, the resonance circuit 280 serves as a communication antenna of the processing unit 206B.

The IC chip 250 performs processing in the same way as the IC chip 250 illustrated in FIG. 6 on the basis of reception voltage transferred from the resonance circuit 280.

Even configured as illustrated in FIG. 8, the processing unit 206B is driven by power obtained from a reception signal (signal transmitted from the resonance unit 204B in the example of FIG. 8) received by the electrode unit 202, processes the reception signal, and transmits a response signal through load modulation as in the configuration illustrated in FIG. 6.

As in the configuration illustrated in FIG. 5, the communication terminal 200 according to the other example is, for example, configured as illustrated in FIG. 7 to perform the processing (signal processing) in (1) and the processing (transmission processing) in (2) for a communication method according to the present embodiment. The communication terminal 200 according to the other example can, thus, improve the convenience of users in the same way as the communication terminal 200 illustrated in FIG. 5.

[3] Use Case by Communication System 1000

Next, a use case will be described which can be implemented by the communication system 1000 including the communication device 100 and the communication terminal 200 configured, for example, as discussed above.

(i) First Use Case: Selective Unlocking of Door

The communication device 100 is installed, for example, on a doorknob that a person (example of dielectrics) touches in the communication system 1000 according to a first use case. In addition, the communication terminal 200 is worn by a person (example of dielectrics). Once a person (example of dielectrics) who is wearing the communication terminal 200 touches a doorknob, dielectric communication is established between the communication device 100 and the communication terminal 200 in a communication method according to the present embodiment. The communication device 100 then selectively unlocks the door in processing based on a result of the communication.

Figure 9:
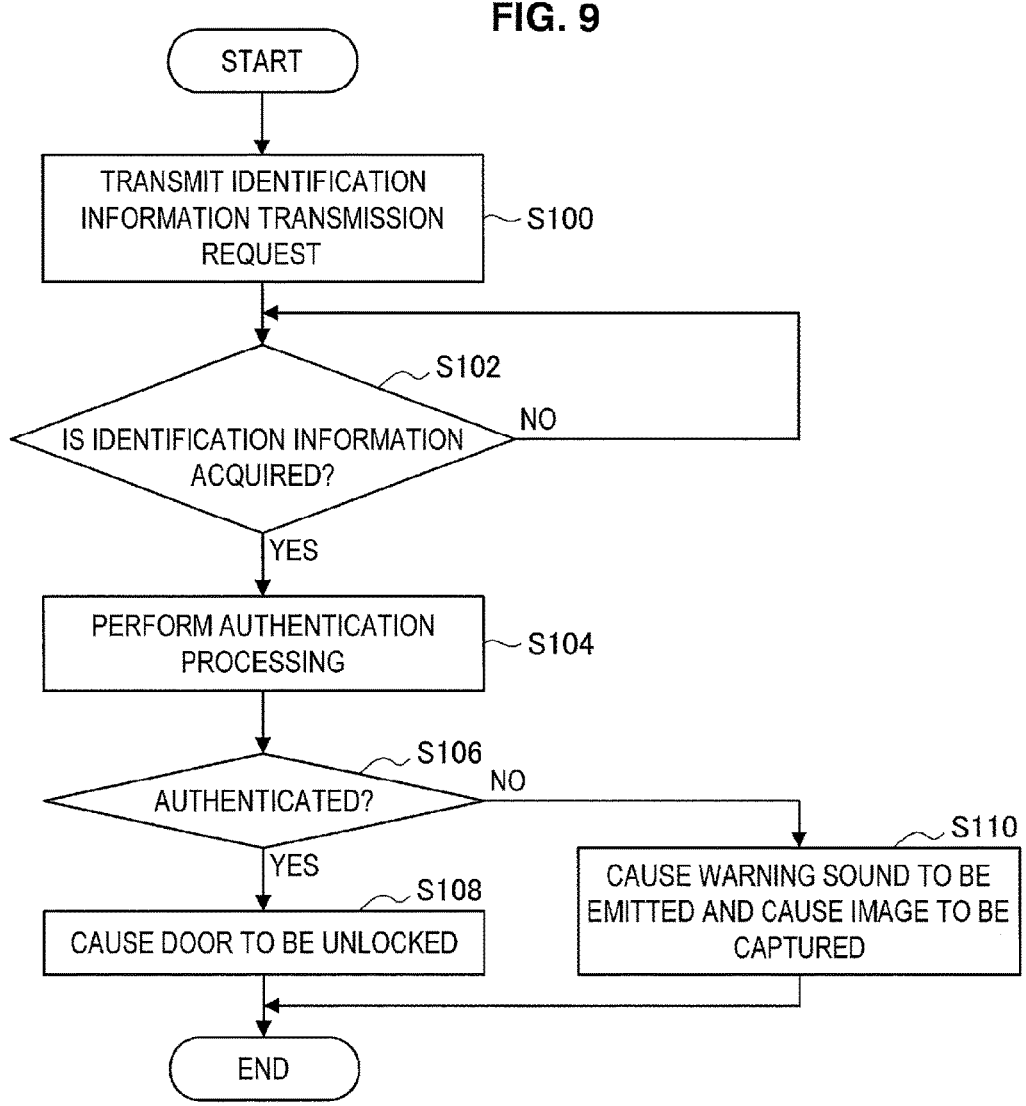
FIG. 9 is a flowchart illustrating an example of processing according to a first use case that can be implemented by the communication system according to the present embodiment.

FIG. 9 is a flowchart illustrating an example of processing according to a first use case that can be implemented by the communication system 1000 according to the present embodiment. Here, FIG. 9 illustrates an example of processing performed by the communication device 100. Each processing illustrated in FIG. 9 is performed chiefly, for example, by the communication unit 106, the communication unit 106, the control unit (not illustrated), and the like.

The communication device 100 transmits an identification information transmission request for requesting transmission of identification information from the electrode unit 102 (S100). The communication device 100 performs, for example, polling, and if a response to the polling is detected, the communication device 100 transmits an identification information transmission request. Additionally, the communication device 100 may transmit an identification information transmission request if a touch on a doorknob is detected on the basis of a result of detection by a touch sensor installed, for example, on the doorknob.

Performing the processing in step S100, the communication device 100 determines whether or not identification information is acquired (S102).

If it is not determined in step S102 that identification information is acquired, the communication device 100 does not have processing proceed until it is determined that identification information is acquired. Additionally, if it has not been determined for a set predetermined time since the processing in step S100 that identification information is acquired, the communication device 100 may, for example, terminate the processing.

To the contrary, if it is determined in step S102 that identification information is acquired, the communication device 100 performs authentication processing with the identification information (S104). For example, if the acquired identification information has been registered in a database, the communication device 100 authenticates the communication terminal 200 corresponding to the identification information. Here, the communication device 100 may, for example, use a database stored in the storage unit (not illustrated) to perform the processing in step S104, or may also communicate with an external device such as a server and use a database stored in the external device to perform the processing in step S104. Additionally, the communication device 100 can perform any authentication processing in step S104 in which the communication device 100 can perform authentication with identification information.

The communication device 100 determines whether or not authentication is normally performed (S106).

If it is determined in step S106 that authentication is performed, the communication device 100 causes a door to be unlocked (S108). Here, unlocking of a door in step S108 is an example of processing corresponding to a result of authentication.

To the contrary, if it is not determined in step S106 that authentication is performed, the communication device 100, for example, causes a warning sound to be emitted from an audio output device and causes an image capturing device to capture an image of a dielectric that touches a doorknob (S110). Here, control exerted by a warning sound and image capturing in step S108 is an example of processing to a result of authentication.

For example, when the communication device 100 performs processing illustrated in FIG. 9, a user (example of dielectrics) who is wearing the communication terminal 200 can have a door unlocked simply by touching the doorknob in the first use case.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, a user (example of dielectrics) who is wearing the communication terminal 200 can have a door unlocked simply by touching the doorknob.

Thus, the communication system 1000 according to the first use case can improve the convenience of users through communication via a dielectric. Additionally, it is needless to say that processing performed by the communication device 100 according to the first use case is not limited to the example illustrated in FIG. 9.

(ii) Second Use Case: Selectively Enabling Wireless Communication Function

The communication device 100 and the communication terminal 200 are worn, for example, by a user (example of a dielectric) in the communication system 1000 according to a second use case. In addition, the communication terminal 200 stores information such as data (example of identification information) indicating, for example, IMSI used for authentication to enable a wireless communication function of the communication device 100 (e.g. the communication terminal 200 includes a subscriber identity module (SIM) card), and once a user operation for enabling the wireless communication function is detected, the communication device 100 performs dielectric communication with the communication terminal 200 in a communication method according to the present embodiment. The communication device 100 then selectively enables the wireless communication function of the communication device 100 in processing based on a result of the communication.

Figure 10:
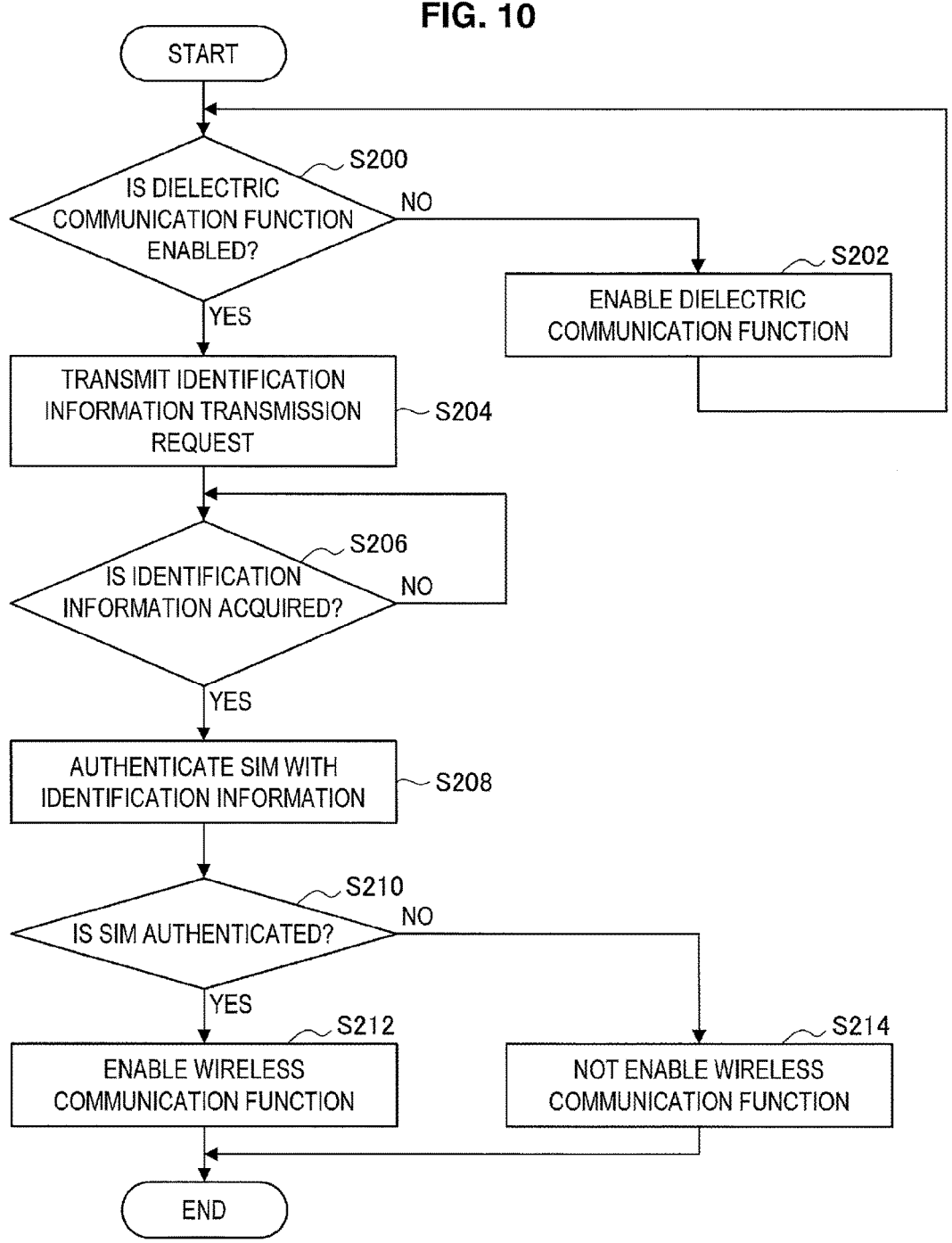
FIG. 10 is a flowchart illustrating an example of processing according to a second use case that can be implemented by the communication system according to the present embodiment.

FIG. 10 is a flowchart illustrating an example of processing according to a second use case that can be implemented by the communication system 1000 according to the present embodiment. Here, FIG. 10 illustrates an example of processing performed by the communication device 100. Each processing illustrated in FIG. 10 is performed chiefly, for example, by the communication unit 106, the communication unit 106 and the control unit (not illustrated), and the like.

The communication device 100 determines whether or not a dielectric communication function is enabled (S200). If it is not determined in step S200 that a dielectric communication function is enabled, the communication device 100 enables the dielectric communication function (S202) and repeats the processing again from step S200.

If it is determined in step 200 that a dielectric communication function is enabled, the communication device 100 transmits an identification information transmission request from the electrode unit 102 as in step S100 of FIG. 9 (S204).

Performing processing in step S204, the communication device 100 determines whether or not identification information is acquired (S206).

If it is not determined in step S206 that identification information is acquired, the communication device 100 does not have processing proceed until it is determined that identification information is acquired. Additionally, if it has not been determined for a set predetermined time since the processing in step S204 that identification information is acquired, the communication device 100 may, for example, terminate the processing.

To the contrary, if it is determined in step S206 that identification information is acquired, the communication device 100 authenticates an SIM with the identification information (S208). Here, examples of the identification information for authentication in step S210 include data indicating IMSI.

The communication device 100 determines whether or not an SIM is normally authenticated (S210).

If it is determined in step S210 that authentication is performed, the communication device 100 enables a wireless communication function (S212). If it is not determined in step S210 that authentication is performed, the communication device 100 does not enable a wireless communication function (S214). Here, selectively enabling a wireless communication function in steps S212 and S214 is an example of processing corresponding to a result of the authentication.

For example, when the communication device 100 performs processing illustrated in FIG. 10, it becomes possible to enable a wireless communication function of the communication device 100, for example, even without any SIM card in the communication device 100 in the second use case.

In addition, a user does not have to replace an SIM card in a communication device in the second use case, which is not true in a traditional case, and the communication device 100 can perform wireless communication with a different telephone number, for example, by a user simply wearing the communication terminal 200 which has different data (example of identification information) indicating stored IMSI.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, it is possible to electively enable a wireless communication function of the communication device 100.

Thus, the communication system 1000 according to the second use case can improve the convenience of users through communication via a dielectric. Additionally, it is needless to say that processing performed by the communication device 100 according to the second use case is not limited to the example illustrated in FIG. 10.

(iii) Third Use Case: Automatic Ticket Gate

The communication device 100 is installed on a floor on which a person (example of dielectrics) walks at a ticket gate, for example, as illustrated in FIG. 1, and the communication terminal 200 is worn by the person (example of dielectrics) in the communication system 1000 according to a third use case. Once a person (example of dielectrics) who is wearing the communication terminal 200 walks on a floor on which the communication device 100 is installed, dielectric communication is established between the communication device 100 and the communication terminal 200 in a communication method according to the present embodiment. The communication device 100 then performs processing for the ticket gate on the basis of a result of the communication.

A user (example of dielectrics) who is wearing the communication terminal 200 simply passes through a ticket gate to allow the communication device 100 (or a ticket gate system including the communication device 100) to perform processing for the ticket gate in the third use case.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, a user (example of dielectrics) who is wearing the communication terminal 200 can have the communication device 100 (or the ticket gate system including the communication device 100) perform processing for the ticket gate.

Thus, the communication system 1000 according to the third use case can improve the convenience of users through communication via a dielectric.

(iv) Fourth Use Case: Vending Machine

The communication device 100 is installed, for example, on a part (such as a selection button) of a vending machine which a person (example of a dielectric) touches in selecting a product in the communication system 1000 according to a fourth use case. In addition, the communication terminal 200 is worn by a person (example of dielectrics). Once a person (example of dielectrics) who is wearing the communication terminal 200 touches a part of a vending machine for selecting a product, dielectric communication is established between the communication device 100 and the communication terminal 200 in a communication method according to the present embodiment. The communication device 100 then performs charge processing with an electronic value stored in the communication terminal 200, and if charging is normally performed, the communication device 100 has the vending machine dispense the selected product for the person (example of dielectrics) who is wearing the communication terminal 200.

A user (example of dielectrics) who is wearing the communication terminal 200 can have the communication device 100 (or a vending machine system including the communication device 100) perform processing for selling products simply by selecting a product in the vending machine in the fourth use case.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, a user (example of dielectrics) who is wearing the communication terminal 200 can have the communication device 100 (or the vending machine system including the communication device 100) perform processing for selling products.

Thus, the communication system 1000 according to the fourth use case can improve the convenience of users through communication via a dielectric.

(v) Fifth Use Case: Individual Management of Domestic Animals

The communication device 100 is installed, for example, on a floor at the entrance of a shed for a domestic animal (example of dielectrics) on which a domestic animal (example of dielectrics) walks in the communication system 1000 according to a fifth use case. In addition, the communication terminal 200 is, for example, attached to a domestic animal (example of dielectrics) or implanted into the body of a domestic animal (example of dielectrics). Once the domestic animal (example of dielectrics) walks on a floor on which the communication device 100 is installed, dielectric communication is established between the communication device 100 and the communication terminal 200 in a communication method according to the present embodiment. The communication device 100 (or an individual management system including the communication device 100) then performs processing for individual management on the basis of a result of the communication.

The domestic animal (example of dielectrics) simply walks on a floor on which the communication device 100 is installed to allow the communication device 100 (or the individual management system including the communication device 100) to perform processing for individually managing domestic animals in the fifth use case. Accordingly, users such as owners of domestic animals who desire to individually manage domestic animals have a burden lessened for individually managing domestic animals in the fifth use case.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, the communication device 100 (or the individual management system including the communication device 100) can perform processing for individually managing domestic animals.

Thus, the communication system 1000 according to the fifth use case can improve the convenience of users through communication via a dielectric.

(vi) Sixth Use Case: Vehicle Authentication Management

The communication device 100 is installed, for example, at a place in a parking lot or a road by which vehicles such as automobiles, motorcycles, and bicycles pass in the communication system 1000 according to a sixth use case. In addition, the communication terminal 200 is attached, for example, to a tire (example of dielectrics) of a vehicle. Once a vehicle having the tire (example of dielectrics) passes by a place in which the communication device 100 is installed, dielectric communication is established between the communication device 100 and the communication terminal 200 in a communication method according to the present embodiment. The communication device 100 (or an authentication management system including the communication device 100) then performs processing for vehicle authentication on the basis of a result of the communication.

A vehicle having the tire (example of dielectrics) simply passes by a place in which the communication device 100 is installed to allow the communication device 100 (or the authentication management system including the communication device 100) to perform processing for vehicle authentication management in the sixth use case. Accordingly, users such as managers of parking lots and managers of roads who desire vehicle authentication management have a burden lessened for vehicle authentication management in the sixth use case.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, the communication device 100 (or the authentication management system including the communication device 100) can perform processing for vehicle authentication management.

Thus, the communication system 1000 according to the sixth use case can improve the convenience of users through communication via a dielectric.

(vii) Seventh Use Case: Manufacture Management

The communication device 100 is installed, for example, on a floor over which manufactured products (example of dielectrics) pass in a production line of a factory in the communication system 1000 according to a seventh use case. In addition, the communication terminal 200 is attached, for example, to a manufactured product (example of dielectrics). Once the manufactured product (example of dielectrics) passes over a floor on which the communication device 100 is installed, dielectric communication is established between the communication device 100 and the communication terminal 200 in a communication method according to the present embodiment. The communication device 100 (or a manufacture management system including the communication device 100) then performs processing for manufacture management of manufactured products on the basis of a result of the communication.

The manufactured product (example of dielectrics) simply passes over a floor on which the communication device 100 is installed to allow the communication device 100 (or the manufacture management system including the communication device 100) to perform processing for manufacture management of manufactured products in the seventh use case. Accordingly, users such as managers of factories who desire manufacture management of manufactured products have a burden lessened for manufacture management of manufactured products in the seventh use case.

As discussed above, the communication terminal 200 according to the present embodiment can process a received reception signal and transmit a response signal via a dielectric even when power is not available from a power supply. That is to say, even when the communication terminal 200 is not capable of obtaining power from a power supply, the communication device 100 (or the manufacture management system including the communication device 100) can perform processing for manufacture management of manufactured products.

Thus, the communication system 1000 according to the seventh use case can improve the convenience of users through communication via a dielectric.

The first to seventh use cases are implemented by the communication system 1000 including the communication device 100 and the communication terminal 200 configured, for example, as discussed above. Additionally, it is needless to say that a use case that can be implemented by the communication system 1000 according to the present embodiment is not limited to the first to seventh use cases.

The description has been made so far by using the communication device as the present embodiment, but the present embodiment is not limited to such a form. The present embodiment can be applied to a variety of apparatuses and equipment including wearable devices such as watches, belts and accessories, devices and facilities according to the first to seventh use cases, communication devices such as cell phones and smartphones, portable game consoles, and the like to which dielectric communication can be applied. In addition, the present embodiment can also be applied to processing ICs that can be incorporated, for example, into the apparatuses and equipment.

In addition, the description has been made by using the communication device as the present embodiment, but the present embodiment is not limited to such a form. The present embodiment can be applied to a variety of apparatuses including, for example, wearable devices, communication devices such as cell phones and smartphones, portable game consoles, and the like to which dielectric communication can be applied. In addition, the present embodiment can also be applied to processing ICs that can be incorporated, for example, into the apparatuses or implanted to living bodies such as domestic animals.

(Program according to Present Embodiment)

[1] Program for Communication Device according to Present Embodiment

A program (program that allows processing such as the processing (transmission processing) in (I) and the processing (signal processing) in (II) for a communication method performed by a communication device according to the present embodiment to be executed) for causing a computer to function as a communication device according to the present embodiment is executed by a computer, which hereby implements a communication system that can improve the convenience of users through communication via a dielectric.

[2] Program for Communication Terminal according to Present Embodiment

A program (program that allows processing such as the processing (signal processing) in (1) and the processing (transmission processing) in (2) for a communication method performed by a communication terminal according to the present embodiment to be executed) for causing a computer to function as a communication terminal according to the present embodiment is executed by a computer, which can hereby improve the convenience of users through communication via a dielectric.

The preferred embodiments of the present invention have been described above with reference to the accompanying drawings, whilst the present invention is not limited to the above examples, of course. A person skilled in the art may find various alterations and modifications within the scope of the appended claims, and it should be understood that they will naturally come under the technical scope of the present invention.

It has been described above, for example, that there are provided a program (computer program) for causing a computer to function as a communication device according to the present embodiment and a program (computer program) for causing a computer to function as a communication terminal according to the present embodiment, but the present embodiment can further provide a recording medium having each of the programs stored therein and a recording medium having both of the programs stored therein.

The above-described configurations show an example of the present embodiment, and naturally belong to the technological scope of the present disclosure.

Additionally, the present technology may also be configured as below.

(1)

A communication terminal including:

an electrode unit configured to cause a dielectric to induce an electric field, and to transmit and receive signals via the dielectric; and a processing unit configured to obtain power from a reception signal received by the electrode unit, to process the reception signal, and to cause a response signal to be transmitted from the electrode unit through load modulation.

(2)

The communication terminal according to (1), further including:

a resonance unit configured to resonate signals at a predetermined frequency, the signals being transmitted and received by the electrode unit.

(3)

The communication terminal according to (2),
wherein the resonance unit includes a first resonance circuit, the first resonance circuit including an inductor and a condenser and performing impedance conversion.

(4)

The communication terminal according to (3),
wherein the resonance unit further includes a second resonance circuit electrically connected to the first resonance circuit, the second resonance circuit having an inductor connected to a condenser in parallel.

(5)

The communication terminal according to any one of (1) to (4),
wherein the processing unit causes a signal including a processing result of processing according to an instruction included in the reception signal and/or information according to the instruction included in the reception signal to be transmitted as the response signal.

(6)

The communication terminal according to (5),
wherein, when the instruction included in the reception signal is an identification information transmission request for requesting transmission of identification information that is usable for identification of the communication terminal, the processing unit causes a signal including the identification information to be transmitted as the response signal.

(7)

A communication device including:
an electrode unit configured to cause a dielectric to induce an electric field, and to transmit and receive signals via the dielectric; and
a communication unit configured to cause a transmission signal to be transmitted from the electrode unit, and to process a response signal received by the electrode unit and transmitted through load modulation for the transmission signal.

(8)

The communication device according to (7), further including:
a resonance unit configured to resonate signals at a predetermined frequency, the signals being transmitted and received by the electrode unit.

(9)

The communication device according to (7) or (8),
wherein the communication unit
causes a signal to be transmitted as the transmission signal, the signal including an identification information transmission request for requesting transmission of identification information usable for identification of an external device, and
processes the response signal, the response signal being transmitted in accordance with the identification information transmission request and including the identification information.

(10)

The communication device according to (9),
wherein the communication unit authenticates the external device on the basis of the identification information, and performs processing corresponding to a result of the authentication.

(11)

A communication method including:
a step of obtaining power from a reception signal received by an electrode unit, and processing the reception signal, the electrode unit causing a dielectric to induce an electric field, and transmitting and receiving signals via the dielectric; and
a step of causing a response signal to be transmitted from the electrode unit through load modulation.

(12)

A communication method including:
a step of causing a transmission signal to be transmitted from an electrode unit that causes a dielectric to induce an electric field, and transmits and receives signals via the dielectric; and
a step of processing a response signal received by the electrode unit and transmitted through load modulation for the transmission signal.

(13)

A program for causing a computer to execute:
a step of obtaining power from a reception signal received by an electrode unit, and processing the reception signal, the electrode unit causing a dielectric to induce an electric field, and transmitting and receiving signals via the dielectric; and
a step of causing a response signal to be transmitted from the electrode unit through load modulation.

(14)

A program for causing a computer to execute:
a step of causing a transmission signal to be transmitted from an electrode unit that causes a dielectric to induce an electric field, and transmits and receives signals via the dielectric; and
a step of processing a response signal received by the electrode unit and transmitted through load modulation for the transmission signal.

(15)

A communication system including:
a communication device; and
a communication terminal configured to communicate with the communication device via a dielectric,
wherein the communication device includes
a device side electrode unit configured to cause the dielectric to induce an electric field, and to transmit and receive signals via the dielectric, and
a communication unit configured to cause a transmission signal to be transmitted from the device side electrode unit, and to process a response signal received by the device side electrode unit and transmitted through load modulation for the transmission signal, and
wherein the communication terminal includes
a terminal side electrode unit configured to cause the dielectric to induce an electric field, and to transmit and receive signals via the dielectric, and
a processing unit configured to obtain power from a reception signal received by the terminal side electrode unit, to process the reception signal, and to cause the response signal to be transmitted from the terminal side electrode unit through load modulation.

REFERENCE SIGNS LIST 100 communication device
102, 202 electrode unit
104, 204A, 204B resonance unit
106 communication unit
110, 210 reference electrode
112, 212 coupling electrode
154, 206A, 206B processing unit
200 communication terminal
214 first resonance circuit
216 second resonance circuit
1000 communication system

The invention claimed is:

1. A communication terminal coupled with a vehicle comprising:
an electrode unit having at least a coupling electrode and a reference electrode configured to cause a dielectric to induce an electric field, and to transmit and receive signals via the dielectric;
a resonance unit comprising a first resonant circuit coupled to the electrode unit and
a resonant antenna circuit coupled to the first resonant circuit;
a processing unit configured to obtain power from a reception signal received by the electrode unit, to process the reception signal, and to cause a response signal to be transmitted from the electrode unit through load modulation; and
a wireless link between the resonant antenna circuit and the processing unit;
wherein the coupling electrode has a surface area less than a surface area of the reference electrode.

2. The communication terminal coupled with a vehicle according to claim 1, further comprising:
the resonance unit configured to resonate signals at a predetermined frequency, the signals being transmitted and received by the electrode unit.

3. The communication terminal coupled with a vehicle according to claim 2, wherein the first resonance circuit includes an inductor and a condenser and performs impedance conversion.

4. The communication terminal coupled with a vehicle according to claim 3,
wherein the resonance antenna circuit is electrically connected to the first resonance circuit, the resonance antenna circuit having an inductor connected to a condenser in parallel.

5. The communication terminal coupled with a vehicle according to claim 1,
wherein the processing unit causes a signal including a processing result of processing according to an instruction included in the reception signal and/or information according to the instruction included in the reception signal to be transmitted as the response signal.

6. The communication terminal coupled with a vehicle according to claim 5,
wherein, when the instruction included in the reception signal is an identification information transmission request for requesting transmission of identification information that is usable for identification of the communication terminal, the processing unit causes a signal including the identification information to be transmitted as the response signal.

7. A communication system comprising:
a communication device; and
a communication terminal configured to communicate with the communication device via a dielectric,
wherein the communication device includes
a device side electrode unit having at least a first coupling electrode and a first reference electrode configured to cause the dielectric to induce an electric field, and to transmit and receive signals via the dielectric, wherein the first coupling electrode has a surface area less than a surface of the first reference electrode, and
a communication unit, including a first communication antenna, a wireless link, and a second communication antenna, configured to cause a transmission signal to be transmitted from the device side electrode unit, and to process a response signal received by the device side electrode unit and transmitted through load modulation for the transmission signal, and
wherein the communication terminal includes
a terminal side electrode unit having at least a second coupling electrode and a second reference electrode configured to cause the dielectric to induce an electric field, and to transmit and receive signals via the dielectric, wherein the second coupling electrode has a surface area less than the surface area of the second reference electrode,
a first resonant circuit coupled to the terminal side electrode unit,
a resonant antenna circuit coupled to the first resonant circuit;
a processing unit configured to obtain power from a reception signal received by the terminal side electrode unit, to process the reception signal, and to cause the response signal to be transmitted from the terminal side electrode unit through load modulation at least to cause the response signal to be authenticated, and
a wireless link between the resonant antenna circuit and the processing unit.

* * * * *